United States Patent
Bercovy

(10) Patent No.: US 6,893,467 B1
(45) Date of Patent: May 17, 2005

(54) KNEE PROSTHESIS

(76) Inventor: Michel Bercovy, 32, Rue Vaugelas, 75015 Paris (FR)

(*) Notice: Subject to any disclaimer, the term of this patent is extended or adjusted under 35 U.S.C. 154(b) by 0 days.

(21) Appl. No.: 10/048,112

(22) PCT Filed: Jul. 25, 2000

(86) PCT No.: PCT/FR00/02133

§ 371 (c)(1),
(2), (4) Date: Apr. 15, 2002

(87) PCT Pub. No.: WO01/06961

PCT Pub. Date: Feb. 1, 2001

(30) Foreign Application Priority Data

Jul. 26, 1999 (FR) .................................. 99-09664

(51) Int. Cl.[7] .............................................. A61F 2/38
(52) U.S. Cl. .................................. 623/20.14; 623/20.21
(58) Field of Search ................... 623/20.14, 20.19, 623/20.21–20.36, 20.15

(56) References Cited

U.S. PATENT DOCUMENTS

| | | | |
|---|---|---|---|
| 3,798,679 A * | 3/1974 | Ewald ..................... | 623/20.31 |
| 3,816,855 A * | 6/1974 | Saleh ...................... | 623/20.31 |
| 3,869,731 A * | 3/1975 | Waugh et al. ............. | 623/20.21 |
| 3,949,428 A * | 4/1976 | Cavendish et al. ........ | 623/20.3 |
| RE29,757 E * | 9/1978 | Helfet ...................... | 623/20.31 |
| 4,209,861 A * | 7/1980 | Walker et al. ............ | 623/20.27 |
| 4,224,696 A * | 9/1980 | Murray et al. ........... | 623/20.29 |
| 4,224,697 A * | 9/1980 | Murray et al. ........... | 623/20.25 |
| 5,330,533 A * | 7/1994 | Walker ...................... | 623/20 |
| 5,609,639 A | 3/1997 | Walker | |
| 5,935,173 A * | 8/1999 | Roger et al. .............. | 623/20.31 |
| 6,165,221 A * | 12/2000 | Schmotzer ............... | 623/20.11 |
| 6,344,059 B1 * | 2/2002 | Krakovits et al. ........ | 623/20.31 |

FOREIGN PATENT DOCUMENTS

| | | |
|---|---|---|
| FR | 2621243 | 10/1987 |
| WO | WO 01/06961 A1 | 2/2001 |

* cited by examiner

*Primary Examiner*—Bruce Snow
*Assistant Examiner*—Cheryl Miller
(74) *Attorney, Agent, or Firm*—Scully, Scott, Murphy & Presser

(57) ABSTRACT

The invention concerns a prosthesis wherein the contact surfaces of the femoral part (i), the insert (3) and the knee joint are defined by the combination of two curves, a spiral-type curve in the saggital plane following an undulating curve (sinusoidal) in the frontal plane. The latter comprises two concave lateral parts and a central dome-shaped convex part, the three parts being connected without any angulation, protuberance, or flat parts or bends and providing continuous medio-lateral contact on the three zones, from complete extension to complete bending, and a concave-convex nesting in the central zone.

7 Claims, 2 Drawing Sheets

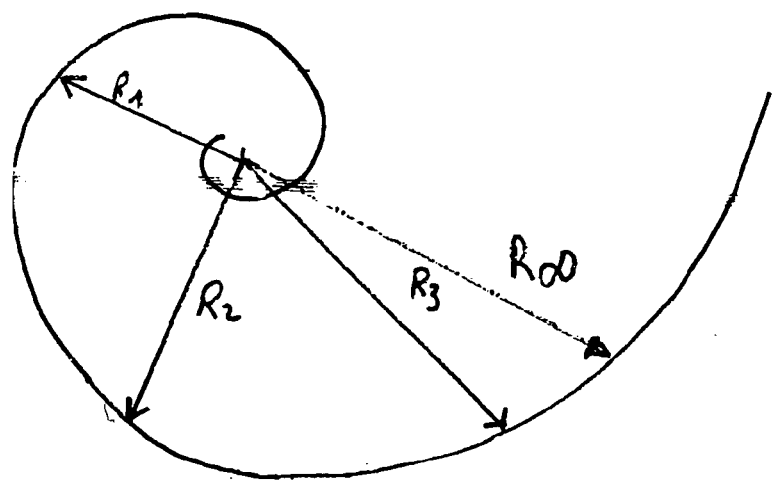
FIG. 1
FIG. 2A
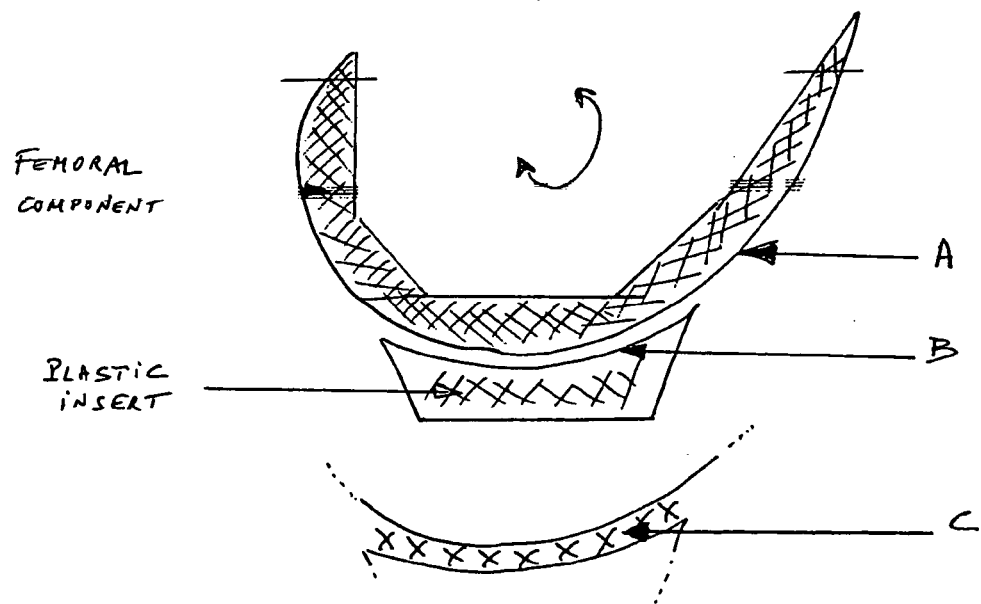
FIG. 2B

KNEE PROSTHESIS

BACKGROUND OF THE INVENTION

1. Field of the Invention

The present invention relates to a novel prosthesis for the knee joint. This prosthesis is more particularly intended to include an arrangement comprising means for optimum contact, stabilization and guidance between the movable components during movements in three directions.

It will be recalled that a knee prosthesis is an implant intended to surgically replace a destroyed knee joint.

A knee prosthesis includes elements integral with the bone, and generally made of metal, and sliding elements, generally made of a plastic material such as polyethylene. The metal elements are:
- a femoral component which more or less reproduces the form of the femoral articulation of the knee; it is fixed to the bone, either directly via a rehabilitation surface, or indirectly by means of an acrylic resin;
- a tibial surface fixed to the upper end of the tibia, either directly, or by means of an acrylic resin; and
- a patellar surface fixed to the posterior face of the patella, either directly or by means of an acrylic resin.

These metal components are generally made of chromium-cobalt, of titanium or of stainless steel, or of other metals and alloys, in particular ceramics.

The sliding and shock-absorbing components separating the metal components are generally made of polyethylene; they can either be made integral with the tibial component or fixed plateau or can be movable relative to the latter with a variable degree of mobility in rotation (horizontal plane), in antero-posterior displacement (sagittal plane), and in medio-lateral displacement (frontal plane); whether they are fixed or movable, the polyethylene sliding components called "inserts" articulate with the femoral component via two femoral condyles, an internal one and an external one, these condyles having a certain congruence with the two respective concave surfaces, called glenoid cavities, of the polyethylene insert. A prosthesis is said to have a movable "plateau" when the insert has a free axial rotation. The prosthesis according to the invention is preferably of this type.

The free axial rotation is a corollary of the congruence; congruence is a major tribologic advantage by virtue of which the pressures and the wear on the polyethylene constituting the insert are low, which gives the prosthesis a longer useful life.

In more recent forms of prostheses, the bearing is effected via three surfaces, a third bearing zone situated between the two condyles being in contact with a median projection situated on the upper surface of the insert. The engagement of these two parts can involve:
- either a third femoral condyle engaging in a third cavity on the upper face of the insert;
- or a stud on the upper face of the insert engaging in a cavity (nest) situated between the two femoral condyles;
- or different forms of cams situated between the femoral condyles and bearing on an elevation on the upper part of the insert.

In all cases, however, there are angulations in a frontal plane, rendering the contact between the components discontinuous.

The anterior part of the femoral prosthesis (trochlea) articulates with the patella by way of a polyethylene medallion. This polyethylene medallion is fixed to the patellar seat or can be movable relative to the latter. There is a certain congruence between the articulation of the femur and the articulation of the patella.

A knee prosthesis does not have to reproduce the exact forms of an anatomical articulation. The reason is that, in the latter, the menisci adjust the congruence between the femoral and tibial components. The cruciate and collateral ligaments co-adapt these components and ensure, by cooperation with the asymmetrical form of the articular surfaces, a relative displacement in the three spatial planes (frontal, sagittal and horizontal). As these different anatomical elements are absent in the prosthetic knee, the latter has to satisfy three types of requirements: the physiology requirements, the tribology requirements, and the stability requirements.

(1) Physiology Requirements

The physiology requirements of the knee must be respected, in particular the displacements and respective positions of the femur relative to the tibia: rolling/sliding with retreat of the point of contact of the femur on the insert during flexion (90°), and advance of the femur during extension (0°), which conditions the moment of action of the patellar tendon, which controls the efficacy of the muscular propulsion and, by this means, the comfort of the patient and the quality of walking, of going up and down stairs, and of standing up from a low position. These relationships must be ensured, during the movements, by the form of the articular surfaces of the prosthetic components (determined by the design of the prosthesis) and in particular by a cam effect between the femur and the insert, in cooperation with balanced tensioning of the collateral ligaments of the knee joint, determined by the action of the surgeon and by ancillary instrumentation respecting this requirement.

(2) Tribology Requirements

The tribology requirements must be respected so that the contact between the femoral components made of metal and the tibial and patellar inserts made of polyethylene do not generate phenomena of wear and tear of the polyethylene. In particular, the contacts must be as congruent as possible, since punctiform or linear contacts or contacts over a small surface generate high pressure in the polyethylene and thus wear and creep of the latter.

2. Discussion of the Prior Art

In certain types of prostheses, the polyethylene insert is fixed relative to the tibia. In this case, the tangential rolling/sliding movements, the shearing movement and all the movements of rotation take place in the contact zone between the femoral condyles and the tibial glenoid cavities. When these contacts are over a small surface area, high pressure can be reached in the polyethylene. Their designers generally recommend a pressure of less than or equal to 10 Mpa in the polyethylene zones where bearing is constant, that is to say in the zones near the walking position. An ideal pressure of 4 Mpa is desirable. However, in the prostheses with a low congruence (linear of punctiform articular surfaces between femur and polyethylene insert), pressure of over 30 Mpa are currently measured, and can even reach 50 Mpa. This leads to rapid degradation of the polyethylene, possibly necessitating further surgery to change the prosthetic implants. A contact surface of greater than 400 $mm^2$ is recommended. The state of the art, in the field of prosthetic joints, has led to the manufacture of prostheses in which the polyethylene inserts are congruent in relation to the femoral surface, a corollary of this congruence being that the insert must be movable in rotation relative to the tibial seat. These implants are referred to as prostheses having a movable plateau. In such cases, the articular congruence can be respected, making it possible to obtain a high degree of surface contact. With this type of prosthesis, pressures of the order of 4 to 8 Mpa are currently obtained in the polyethylene, which promotes the useful life of the latter.

Various congruent prostheses exist, but they all have two major disadvantages, which the present invention aims to correct:
the congruence of the contact between the condyles and the tibial glenoid cavities is present particularly near extension but diminishes during flexion;
the congruence is envisaged in only one plane: the sagittal plane; thus, considerable stresses can arise in the contact zones during movements of inclination or lift-off, or rotation, or in combination in these three directions, particularly when the surfaces include angulations.

To obviate this, the various surfaces must be tangential in relations to one another in the two spatial planes (sagittal and frontal) in order to permit sliding movements without sudden stops and without angular contacts in these three directions.

(3) Stability Requirements

The stability of the knee in which a prosthesis is fitted can be respected by different mechanisms:
retention of the two cruciate ligaments;
retention of only the posterior cruciate ligament, although it has been shown that in this case the antero-posterior displacement does not have satisfactory kinematics;
finally, stabilization of the prosthesis by a central mechanism intended to guide the femur in relation to the tibia.

This latter type of mechanism is in fact the most effective for keeping the stability in accordance with the kinematics of the knee, and it is a device of this type with which the present invention is concerned.

The state of the art in this field includes several types of mechanisms:
the most traditional is that of a rod which comes into contact with a vertical central stud of variable shape;
other mechanisms use a cam cooperating with a central abutment which has a profile complementing this cam; for example, the third and central femoral condyle; situated between the two lateral condyles;
in other prosthesis configurations, there can be a third, central condyle which itself is in the form of a transverse cylinder which is engaged in a transverse cylinder ending at its front part in the form of a cam.

A disadvantageous effect of this latter configuration is a total absence of freedom of antero-posterior movement between the femoral component and the tibial insert when the cylinder has the same transverse axis as the two lateral condyles. It is therefore a mechanism of the so-called hinge type, which can be responsible for considerable pressures in the articulation between the patella and the femur. The mechanism of rolling/sliding is not respected and one of the consequences can be the existence of considerable patellar pain. The recovery of a certain forward/rearward mobility in the zone of contact between polyethylene insert and tibial plateau is not sufficient to overcome this disadvantage; this mobility situated at a different level than normal generates a parasite movement referred to as "roll forward", during which the tibia moves back in flexion relative to the femur, which can lead to disengagement of the prosthetic components.

In a configuration of this type of prosthesis (see WO 98/46171 A), the median projection has on its upper face a guide curvature, bearing on a complementary surface situated between the two femoral condyles producing a cam effect, which develops an optimum displacement of the femur relative to the tibia. However, the engagement of this device in the frontal plane reproduces a broken curve, a source of shocks, of angular contact (edge contact), sudden stops, and, thus, mechanisms which can cause loosening of the prosthesis.

The present invention is therefore based on a prosthesis with movable plateau, the plateau or insert being totally congruent in the transverse direction via its upper surface with the articular surfaces of the femur and, via its lower face, with the upper face of the metal seat implanted in the tibia.

Among the currently existing prostheses with congruent movable plateau, most have a congruence in the zones near extension, but this congruence diminishes considerably upon flexion on account of the progressive decrease in the radii of curvature of the condyles in the posterior part of the articulation, whereas the radius of curvature of the tibial plateau remains constant. This is due to the polycentric radius of the condyle in the sagittal plane.

Other implants have large contact surfaces from extension to flexion. However, in these designs, the different sagittal planes (in the plane XY) are offset in relation to one another, which, when seen from the front, translates into a broken line which is likely to generate high stress peaks in the polyethylene, as well as transmission of abnormally high stresses, shocks and vibrations to the sites of fixation of the prosthesis during movements of lift-off/lateral inclination.

In general, the bearing of knee prostheses is effected by the contact between the femoral condyles and the tibial glenoid cavities, with a medial bearing and a lateral bearing. Since the mechanical axis of the body running from the center of gravity of the body to the contact of the foot with the ground passes medially in relation to the knee joint, the bearings on both the medial and lateral compartments of the knee are asymmetrical, creating several sources of problems.

One of these lies in the fact that a loosening moment is created by means of a compression in the internal compartment which is much greater than the compression in the external compartment. For this reason, the external compartment of the knee tends to lift at the level of its tibial fixation and lead to a possibility of separating of the latter, the source of mobilization of the prosthesis, which can result in deterioration and a new surgical procedure.

Another source of problems lies in the fact that, between the bearing phase and the oscillating phase of walking, there is a separating of the femoral metal component relative to the polyethylene insert, which in English is referred to by the term lift-off. This lift-off is seen principally between 40 and 70° flexion of the knee, principally in the zone from 50 to 70°. This generally involves the separating of the lateral condyle relative to the lateral tibial plateau. This lift-off, which exists physiologically (about 1.8 mm) can attain amplitudes of several millimeters, sometimes 5 mm or more, in the case of certain prostheses.

In the form of bearing elaborated according to the invention, by means of concave-convex engagements in the frontal and sagittal planes, the bearing is effected via the lateral condyles and on the central dome, and on the oblique lateral slopes of this dome, which, as will be seen below, is one of the main originalities of the invention.

SUMMARY OF THE INVENTION

In the concept proposed according to the invention, the resultant of the transmissions of the stresses is preferably directed to the central part of the tibial seat, about its central element of fixation which is called a stem and is fitted at the center of the upper end of the tibial bone. The aim of this type of transmission is to reduce as much as possible the medio-lateral torque effect which is responsible for the loosening or for predominant wear of one of the two compartments.

The concave-convex engagement in the frontal and sagittal planes between the central depression of the femur and the torus (the median projection of the insert) has the benefit of offering a congruent and progressive bearing during the lift-off movements, irrespective of the angle of flexion of the knee.

This form of contact between the femoral metal component and the polyethylene insert additionally makes it possible to vary the contacts in a continuous manner via the progressive engagement of the contact surface, avoiding the shocks and vibrations which, when they are transmitted to the anchoring points of the metal components in the tibial or femoral bone, are a source of vibrations which once again favor the loosening of the prosthetic components, which leads to the latter being changed.

The present invention aims to make available a knee prosthesis which does not have the above-mentioned disadvantages of the prostheses of the prior art.

The prosthesis according to the invention has two objectives:
  the congruence intended to protect the longevity of the polyethylene used and to diminish its wear;
  kinematics intended to give a functioning which is comfortable for the patient.

Congruence
  a congruence with a large contact surface between the femoral component and the insert, irrespective of the angle of flexion, makes it possible to reduce the pressures exerted on the polyethylene;
  the congruence must diminish during flexion, the large contact surface being necessary in the bearing sector from 0 to 60°, but the sector of flexion beyond 90° does not require a large contact surface because:
  the use of this sector is more rare;
  congruence extended to all degrees of flexion, in particular beyond 90°, results in a prosthesis which is subject to considerable stress, hence a risk of excessive stressing of the anchoring points;
  the high level of surface congruence is necessary, but without angular contact and without flat parts or bends of the tenon and mortise type involved in the movements of LIFT-OFF or lateral inclination, irrespective of the angle of flexion:
  This is frontal congruence.

Kinematics
  the kinematics must promote the lever arm of the extensor apparatus (efficacy of the work of the quadriceps muscle by way of the patella and the patellar tendon) in order to permit an effective force when going up or coming down stairs. This is obtained by an anterior offset of the patellar bearing on the trochlea in extension.
  the kinematics must respect the true rolling/sliding of the knee. This is defined in the following way: the point of contact of the femoral component relative to the insert is a few millimeters in front of the center of this insert in extension at 0° and retreats several mm behind the center of the insert when the flexion exceeds 15 to 20°, without the femoral component and the femoral bone segment displacing rearward relative to the tibial component or the tibial bone segment. This is distinguished from false rolling/sliding in which the femoral component and the femoral bone retreat under a cam effect relative to the tibial component of the prosthesis or relative to the tibial bone, which phenomenon must be avoided since it generates:
  1) abnormally high pressures on the polyethylene of the patella and of the insert, sources of early wear and pain;
  2) movements of rearward translation of the femur on the insert, generating delamination under the surface of the polyethylene and hence early wear of the latter.

In order to meet these objectives, the present invention proposes a novel geometry of the surfaces of the femoral component and of the insert. More precisely, the invention concerns a knee joint prosthesis which comprises:
  a system with three zones of bearing between the femoral component and the insert;
  a system having medio-lateral continuity of the contact between the bearing surfaces of the femoral component and of the insert;
  a succession of concave or convex surface segments having the form of a spiral in profile;
  the concave parts of the femoral surface corresponding to convex tori of the surface of the insert;
  in the frontal plane, a succession of condyle/insert engagements, being concave-convex, then convex-concave, then concave-convex, going from the medial condyle to the lateral condyle;
  in the sagittal plane, the three femoral surfaces-medial, central and lateral—have a downwardly directed convexity, while the three surfaces of the insert have an upwardly directed concavity, so as to have a central zone of saddle shape but a continuous medio-lateral contact.

It is also an object of the invention to make available a knee prosthesis in which the general shape of the three zones-lateral, central and medial—of the femoral component are determined by a spiral curve in the sagittal plane, the general shape of the three zones-lateral, central and medial—of the insert being also determined by a spiral curve in the sagittal plane, the generating spiral curve of the insert being derived from the generating spiral curve of the femoral component. These two spiral curves are calculated with the aim of reproducing the true rolling/sliding according to the definition given above.

It is also an object of the invention to make available a knee prosthesis in which the congruence of the articular surfaces between the femoral condyles and the polyethylene insert in the frontal plane is ensured by a succession of continuous curved surfaces in the three bearing zones, the curved surfaces being interconnected without any discontinuity or sharp edge or bend or flat part, thereby permitting displacement in lift-off, in translation and in inclination in the frontal plane between the femoral component and the insert, during which the contact surface will always be congruent, irrespective of the angle of flexion.

Finally, it is an object of the invention to make available a knee prosthesis in which the bearings are transmitted in a continuous manner from the medial part to the lateral parts of the prosthesis during the walking cycle, with loading free of jolts, without risks of vibration or of sudden transmission of stresses, affording the patient a comfortable effect of suppleness and ensuring that the patient does not experience shocks.

To achieve this functionality, which thus entails an optimum compromise between kinematics and congruence, the invention relates more specifically to the geometric form of the surfaces of the femoral component and of the insert.

To this end, the invention relates to a knee prosthesis of the type comprising a femoral component which is generally of metal and can be implanted in the femur, a tibial component which is generally of metal and can be implanted in the tibia, and an intermediate component or insert which is made of a plastic material such as polyethylene and is interposed between the tibial component and the femoral component, the insert being able to be made rigidly integral with the tibial component or movable in rotation about a vertical axis relative to the latter, the femoral component comprising, on the one hand, two lateral parts with condylar surface which can bear and move in two lateral cavities of appropriate profile in the insert, and, on the other hand, a hollowed central part arranged between the lateral condylar parts and able to bear on a projecting central part of the insert, the projecting central part of the surface of the insert directed toward the femoral component having a convex shape, seen from the front, and a concave shape, seen in profile, while the intercondylar arch of the femoral component has a concave shape, seen from the front, and a convex shape, seen in profile, from the front to the rear of the femur, allowing it to straddle the projecting part of the insert during its relative displacements and to cooperate with it in the manner of a cam, where the surfaces of the femoral component and of the insert designed to come into contact during the relative movements of the two components do not have any discontinuity or sharp edge and cooperate by straddling of concave parts and convex parts during the totality of these movements in each of the sagittal and frontal planes, this prosthesis being characterized in that, in cross section in a frontal plane, the surface of the insert directed toward the corresponding surface of the femoral component is a curve which includes an undulating central portion whose convexity is directed toward the femoral component and which connects tangentially on each side to a hollowed part having a shape corresponding substantially to that of the associated condylar part of the femoral component, the whole forming an undulating curve without any discontinuity or sharp edge, of the general type of a sinusoid, and in that, in cross section in a frontal plane, the surface of the femoral part directed toward the corresponding surface of the insert is a curve which includes an undulating central portion whose concavity is directed toward the insert and which connects tangentially on each side to the condylar parts of the femoral component, the whole forming an undulating curve without any discontinuity or sharp edge, of the general type of a sinusoid.

More precisely, the surfaces of the femoral component and of the insert which are intended to come into contact during the relative movements of the two components are surface portions which have no discontinuity or sharp edge or flat part or bends and which cooperate by straddling of concave parts and convex parts during the totality of the movements in each of the sagittal and frontal planes, irrespective of the angle of flexion.

The surfaces of the femoral component and of the insert arranged opposite each other are substantially complementary, except for clearance or laxity intended to permit the movements:

in a frontal plane: movement called lift-off, that is to say sliding lift and angulation of a condyle and angulation, with a contact remaining congruent between the femoral component and the insert both in the lateral cavity of the insert and on all or part of the central dome, irrespective of the angle of flexion;

in a sagittal plane: a movement of flexion with preferably a natural roll/glide of the femoral component on the insert, that is to say a displacement of the point of contact of the femur on the insert from a few millimeters in front of the center of the insert, in position of extension 0, to a few millimeters behind the center of the insert, in the flexed position, but without displacement of the femoral component itself, or of the bone segment which carries it, relative to the tibial component (absence of translation);

in a horizontal plane: rotation relative to a vertical axis, of which the amplitude varies depending on whether the insert is movable in rotation or not relative to the tibial component; according to the invention, the insert is preferably free on axial rotation.

More precisely, seen in cross section through a frontal plane, the surface of the insert directed toward the corresponding surface of the femoral component and coming into continuous contact in the medio-lateral (transverse) direction with the latter comprises two lateral curve segments with the concavity directed upward and one central curve segment whose convexity is directed toward the femoral component, the convexity of the central part connecting tangentially on each side to the concave parts with a profile which corresponds substantially to the associated condylar part of the femoral component, the whole forming a curve direction discontinuity or sharp edge, like a sinusoid.

Likewise, seen in cross section in a frontal plane, the femoral part has a complementary profile from the front to the rear of the condyles. In other words, there is a convex medial curve directed downward, then a central concavity straddling the central part of the insert, then a lateral convexity directed downward, these three curve segments coming into continuous contact in the medio-lateral (transverse) direction with the corresponding surfaces of the insert.

A prosthesis of the prior art (see U.S. Pat. No. 4,470,158) likewise comprises a femoral component defined by two generating curves, a frontal curve passing through a sagittal curve. However, this prior art prosthesis differs fundamentally from that of the present application in that:

the frontal generating curve is a geometric element of the design but does not correspond totally to the zone of contact between the prosthetic components (femur and insert) because the femoral component of this prosthesis has only two conventional condyles separated by a discontinuous zone (notch) whereas, according to the present invention, there is total continuity from one margin of the femoral component to the other.

In said US patent, the generating curve portion called K3 is a design element, but not a zone of continuous material for bearing of the femoral component on the insert, like the central radius of the prosthesis according to the invention. The frontal generating curve of the US prosthesis passes through a polycentric sagittal curve which comprises four segments of different radii from front to back, whereas, according to the present invention, the frontal zone passes through a spiral generating curve.

In practice, in the prosthesis according to the present invention, the precise form to adopt for the spiral curvatures of the insert and of the central surface of the femoral component in the sagittal plane is defined from X-rays of the knee of the patient in various positions of flexion, in such a way as to reproduce as exactly as possible the displacement of the point of contact of the natural joint in true rolling/sliding, that is to say a displacement of the point of contact without displacement of the bone segments or of the prosthetic components.

Likewise, the precise form to adopt for the curve in the frontal plane is defined by the need for an angulation of approximately 5° between the femoral component and the insert during the lateral lifting referred to as lift-off (or varus-valgus).

This distinguishes the prosthesis according to the invention from that of WO 98/46171 A in which, although there is a continuity with three bearing surfaces—two condyles and an intercondylar cam—the conformity in the frontal plane concerns only the lateral cavities of the insert and the corresponding condyles, but not the central part.

BRIEF DESCRIPTION OF THE DRAWINGS

The attached diagrammatic drawings illustrate an embodiment of the invention in greater detail. They do not of course imply any limitation. In said drawings.

DETAILED DESCRIPTION OF THE INVENTION

Figure 3A:
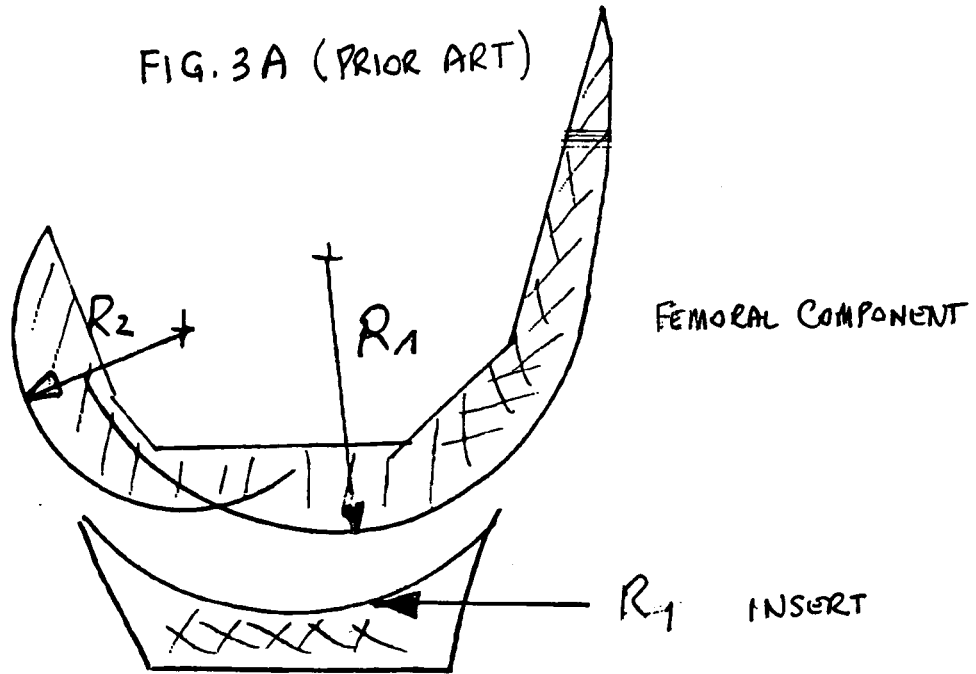
FIG. 3 shows sections through a frontal plane of the opposite contact surfaces of the insert and of the femoral component.
Figure 3B:
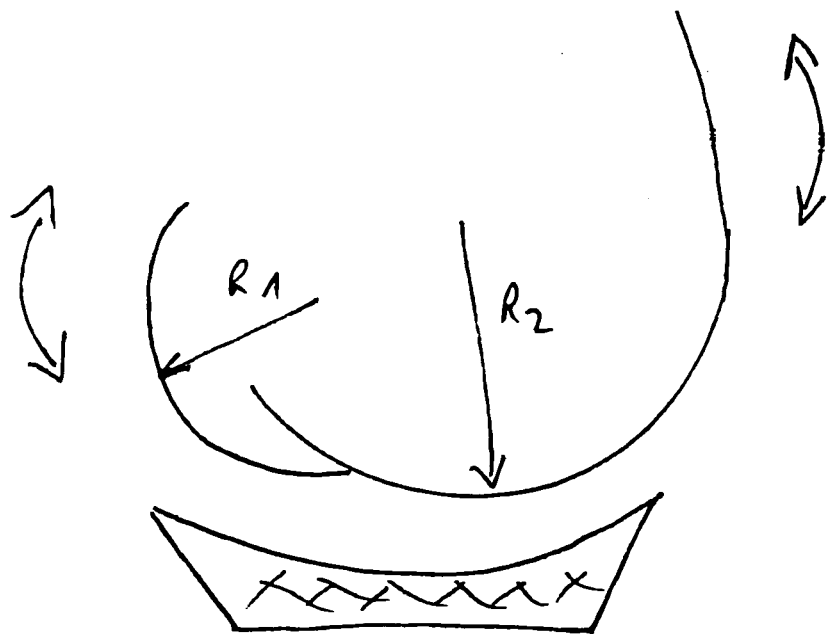
Figure 1:
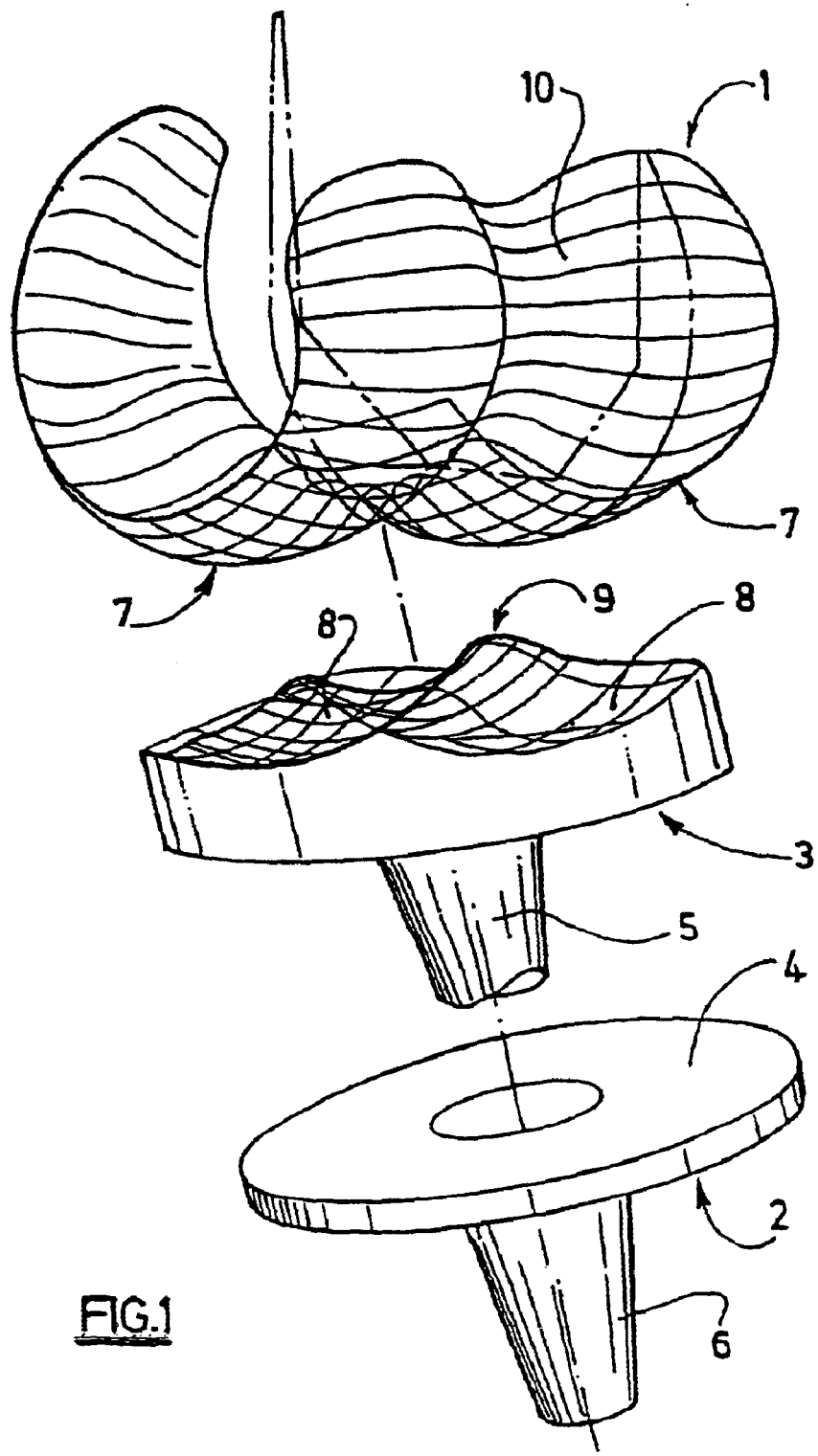
FIG. 1 is an exploded perspective view of a knee prosthesis according to the invention.

The knee prosthesis illustrated in FIG. 1 comprises a femoral component 1 which is generally of metal and can be implanted in the femur of the patient, a tibial component 2 which is also of metal and can be implanted in the tibia of the patient, and an insert 3 which is generally of a plastic material such as polyethylene.

The insert 3 bears on a plateau 4 of the tibial component 2 and can be fixed in position on the latter or, as is shown in the drawing, can be movable in rotation relative to the plateau 4 about an axis which, in the position of use of the prosthesis, is disposed vertically. For this purpose, the insert 3 here comprises, projecting from its surface directd toward the component 2, a stud 5 which is engaged in a hollow central stem 6 of the tibial component 2, in a manner known per se.

In a conventional manner, the femoral component 1 comprises two lateral condylar parts 7 whose cross section, through a sagittal plane, has the form of a spiral, the exact geometric nature of which is not relevant to the present invention.

The femoral component 1 is intended to be displaced preferably in a rolling/sliding movement, with a tolerance of a few millimeters in the condylar parts 7, on hollowed parts 8 in that face of the insert 3 directed toward the component 1, which have substantially corresponding shapes, also with a spiral profile when seen in section in a sagittal plane.

According to the invention, the insert 3 has, in its central part, a projecting dorsal part 9 forming a cam which, seen from the front (see FIGS. 2 and 3), has an undulating profile whose convexity is directed toward the femoral component, whereas, when seen from the side, it has a concave profile, this projecting part 9 having no discontinuity or angulation or sharp edge, and connecting tangentially in all directions to the contiguous surfaces 8, also without discontinuity, angulation or sharp edge. The intercondylar arch 10 of the femoral component 1 has a shape substantially complementing that of the part 9 of the insert which it straddles from extension to complete flexion and it too connects tangentially to the condylar parts 7 in all directions, without discontinuity, angulation or sharp edge.

This straddling by the femoral part on the insert 3 thus translates into a concave-convex engagement of the two components in a sagittal plane, and a concave-convex engagement of the two components in a frontal plane, nevertheless permitting an antero-posterior translation of the femoral component 1 relative to the insert 3, guiding being provided by the engagement of the projecting part 9 of the insert, whose upper surface in section in a sagittal plane is concave, in the intercondylar arch 10 of the femoral component 1, and whose median lower face is convex in a sagittal plane, this process taking place throughout the movement of flexion extension.

This median concave-convex engagement also permits the arrest of abnormal forward or rearward displacements (subluxation or luxation) of the femur relative to the tibia and vice versa, with the advantage of this arrest being progressive, on account of the continuity of the surfaces in mutual contact.

As has been explained above, the complementary nature of the surfaces of parts 9 and 10 which come into mutual contact during the relative displacement of the femoral component 1 and of the insert 2 is not absolute and must provide some play or "laxity" permitting a sliding take-off movement, or lift-off, of a condylar part, with an amplitude of approximately 2 to 5 mm in the frontal plane, an overall antero-posterior laxity or "drawer", in a sagittal plane, also of between 2 and 5 mm, and a rotation about a vertical axis, in a horizontal plane, of the order of 8°, but which can be less when the insert 3 is itself movable relative to the tibial component 2.

As has been mentioned above, the precise shape of the projecting part 9 forming a cam in the sagittal plane is determined by X-rays of the knee joint, bent in a large number of different positions, and it is not defined by a precise mathematical equation. This cam is such that, at an angle of flexion of 0°, the center of the bearings of the femur on the insert is a few millimeters in front of the center of the insert and such that it is a few millimeters behind this center starting from a certain degree of flexion of between 15° and 20°.

The different surfaces respectively of the femur and of the insert are simply tangential to each other in all planes, without any zone of rupture, the contact surface moving from the front to the rear of the insert, as physiology demands.

Figure 2:
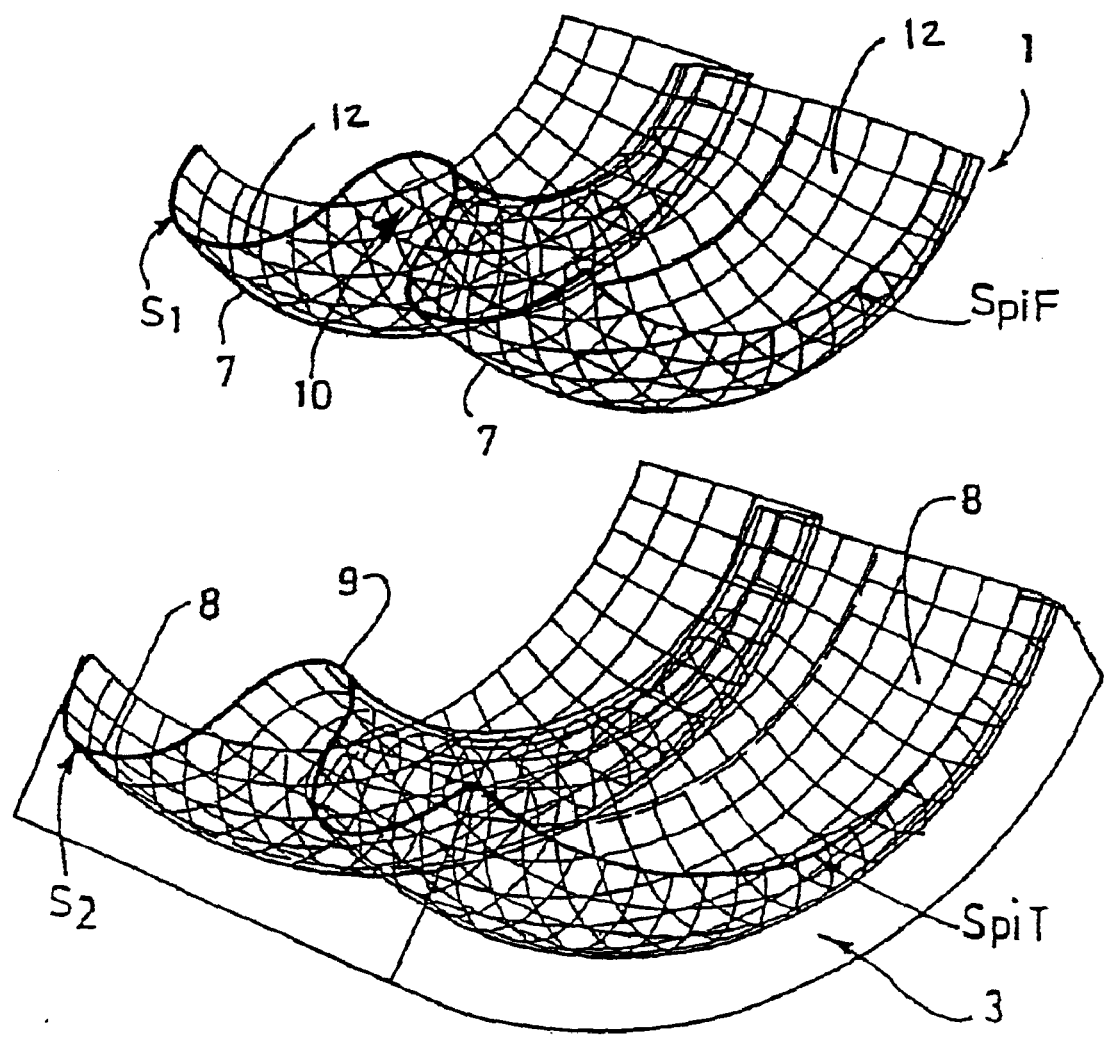
FIG. 2 is a diagrammatic view, on a larger scale, illustrating the substantially complementary shape of the opposite contact surfaces of the insert and of the femoral component.

FIG. 2 shows the surfaces generated by the two curves S1 and Spi F for the femoral contact surface, and S2 and Spi T for the contact surface of the insert.

As has been indicated above, the curves Spi F and Spi T have a spiral form, without implying a precise mathematical definition. Likewise, in cross section in a frontal plane, the contact surface S1 of the femoral component 1 and the contact surface S2 of the insert (see FIG. 3) have a sinusoidal profile, without this term implying a precise mathematical equation, and the different portions of the two curves comprise different portions of the two curves comprise different radii of curvature, such as R1, R2, R3, R'1, R'2, R'3 and connect tangentially to each other.

It will be noted that the hollowed central part 12 of the femoral component 1 connects to the lateral parts 7 of this component 1 via a radius of curvature $R_2$ which is constant from front to rear. Likewise, the convex central part 9 of the insert 3 directed toward the femoral component 1 connects to the hollowed lateral parts 8 of this insert via a radius of curvature $R'_2$ which is constant from front to rear.

The prosthesis according to the invention has the advantage of respecting the physiological kinematics of the knee, that is to say the preferred rolling/sliding movement of the joint, with retreat of the point of contact of the femur on the insert from extension to flexion, which optimizes the moment of action of the extensor apparatus and, consequently, the force of propulsion of the knee, when walking upward, when walking downward, and when standing up.

It also has the advantage of:
- maintaining a large contact surface during the flexion of the knee, which, as a corollary, generates a low pressure in the polyethylene and thus minimal wear of the prosthesis;
- maintaining congruence during the movements of inclination in the frontal plane, thus an absence of shocks and mechanisms of tearing or loosening;
- conferring on this device a good stability of the components relative to one another during the rearward displacements and lateral inclination;
- maintaining a total medio-lateral contact surface from extension to complete flexion, the surface decreasing progressively by the contacting of spiral curves.

What is claimed is:

1. A knee prosthesis, which is implantable in the knee joint of a patient, said prosthesis comprising a femoral component (1) which is implantable in the femur of the knee joint; a tibial component (2) which is implantable in the tibia of the knee joint; and an intermediate insert (3) which is interposed between the tibial component and the femoral component of said prosthesis, said insert being selectively rigidly integral with the tibial component or movable in rotation about a vertical axis relative to the tibial component, said femoral component comprising two lateral parts (7), each with a condylar surface which bears against and is movable in two lateral cavities (8) of a complementary profile provided in the insert, and includes a hollowed central part (10) arranged between said lateral parts and which bears on a projecting central part (9) of the insert, the projecting central part (9) of the insert (3), which is directed toward the femoral component (1) having a convex shape in a frontal plane, and a concave shape in a sagittal plane, the hollowed central part (10) of the femoral component (1) having a concave shape in a frontal plane, and a convex shape in a sagittal plane extending from the front to the rear of the femur of the knee joint, so as to facilitate the femoral component (1) straddling the projecting central part (9) of the insert during relative displacements thereof and to cooperate cam-like therewith, said knee prosthesis having the femoral component (2) and the insert (3) come into mutual surface contact during the relative movements between said femoral component and said insert in the absence of any discontinuities, flats and sharp edges and cooperate through the straddling of any concave parts and convex parts of said femoral component and of said insert during the entirety of these movements within, respectively, each of the sagittal and frontal planes, wherein transversely in a frontal plane, the insert (3), which is directed towards the mutual contact surface of the femoral component and coming into continuous medio-lateral contact with the femoral component (1) is a curve (S2) which includes a projecting central part (9) having an inwardly curved central portion possessing a convexity which is directed towards the femoral component and which connects tangentially on opposite sides thereof to lateral cavity (8) having a shape corresponding substantially with that of a therewith associated condylar part of the femoral component (1), forming an undulating curve across the entire extent thereof in the absence of discontinuities, flats and sharp edges in all directions, in a generally sinusoidal configuration, and wherein transversely in a frontal plane, the surface of the femoral component (1), which is directed towards the complementary surface of the insert coming into continuous medio-lateral contact with the insert (3) defines a curve (S1) which includes a hollowed central part (10) having an undulating shape with a concavity which is directed towards the insert and which connects tangentially on opposite sides thereof to the lateral parts (7) of the femoral component (1), forming an undulating curve, in the absence of any discontinuities, flats and sharp edges, of generally a sinusoidal configuration across the entirety thereof, which follows the surface of the femoral component and of the insert from the most frontal parts to the rearmost parts thereof, the mutual contact surface of the femoral component being defined by the combination of a spiral curve, said spiral curve consisting of a plurality of continuously varying radii along the extent thereof extending in sagittal planes following from medial to lateral an undulating sinusoidal-like curve in the frontal plane, the insert (3) having a spiral curve, said spiral curve consisting of a plurality of continuously varying radii along the extent thereof in the sagittal plane following a sinusoidal-like curve extending in the frontal plane, in the absence of any discontinuities, flats and sharp edges, in correlation with the configuration of at least a portion of the spiral curve in all sagittal planes of said femoral component, said two femoral component and insert surfaces being in a concave-convex engagement in each of said two planes, whereby the two mutual contact surfaces provide for a continuous transverse medio-lateral contact from complete extension to complete flexion of the prosthesis.

2. The prosthesis as claimed in claim 1, wherein the lateral parts and the hollowed central part (10) of the femoral component (1) extending transversely through at least one sagittal plane, have the shape of a spiral curve of any geometrical form, said spiral curve consisting of a plurality of continuously varying radii along the extent thereof, and wherein extending transversely through a sagittal plane, the complementary lateral parts (8) and the projecting central part (9) of the insert (3) also have the shape of a spiral curve of any geometrical form, said spiral curve consisting of a plurality of continuously varying radii along the extent thereof, which are at least partly the shape of the spiral curve of the femoral component.

3. The prosthesis as claimed in claim 1, wherein the projecting central part (9) of the insert (3) and the hollowed central part (10) of an intercondylar space of the femoral component (1) have, in the sagittal plane, two curvatures which cooperate cam-like, said cam-like motion being such that, at an angle of flexion of 0°, the center of the bearings of the femoral component against the insert is a few millimeters in front of the center of the insert (3), such that said center retreats a few millimeters behind the center of the insert, as the prosthesis enters into flexion.

4. The prosthesis as claimed in claim 1, wherein said prosthesis comprises:
- a system with three zones of bearing between the femoral component (1) and the insert (3);
- a system having medio-lateral continuity of the contact between the bearing surfaces of the femoral component (1) and of the insert (3);
- a succession of concave or convex surface segments having the form of a spiral in profile;

the concave surface segments of the femoral component corresponding to convex tori on the bearing surface of the insert;

the convex surface segments of the femoral component corresponding to concave tori on the bearing surface of the insert (3);

in the frontal plane, a succession of fitting engagements of the femoral component in the insert, which are successively convex-concave, then concave-convex, extending from the medial condyle to the lateral condyle; and the three surfaces of the femoral component (1), medial, central and lateral, defining, when viewed in the sagittal plane, a downwardly directed convexity, whereas the three surfaces of the insert (3) have an upwardly directed concavity, so as to provide a central zone of saddle shape but facilitating a continuous medio-lateral contact.

5. A knee prosthesis, which is implantable in the knee joint of a patient, said prosthesis comprising a femoral component (1) which is implantable in the femur of the knee joint; a tibial component (2) which is implantable in the tibia of the knee joint; and an intermediate insert (3) which is interposed between the tibial component and the femoral component of said prosthesis, said insert being selectively rigidly integral with the tibial component or movable in rotation about a vertical axis relative to the tibial component, said femoral component comprising two lateral parts (7), each with a condylar surface which bears against and is movable in two lateral cavities (8) of a complementary profile provided in the insert, and includes a hollowed central part (10) arranged between said lateral parts and which bears on a projecting central part (9) of the insert, the projecting central part (9) of the insert (3), which is directed toward the femoral component (1) having a convex shape in a frontal plane, and a concave shape in a sagittal plane, the hollowed central part (10) of the femoral component (1) having a concave shape in a frontal plane, and a convex shape in a sagittal plane extending from the front to the rear of the femur of the knee joint, so as to facilitate the femoral component (1) straddling the projecting central part (9) of the insert during relative displacements thereof and to cooperate cam-like therewith, said knee prosthesis having the femoral component (2) and the insert (3) come into mutual surface contact during the relative movements between said femoral component and said insert in the absence of any discontinuities, flats and sharp edges and cooperate through the straddling of any concave parts and convex parts of said femoral component and of said insert during the entirety of these movements within, respectively, each of the sagittal and frontal planes, wherein transversely in a frontal plane, the insert (3), which is directed towards the mutual contact surface of the femoral component and coming into continuous medio-lateral contact with the femoral component (1) is a curve (S2) which includes a projecting central part (9) having an inwardly curved central portion possessing a convexity which is directed towards the femoral component and which connects tangentially on opposite sides thereof to lateral cavity (8) having a shape corresponding substantially with that of a therewith associated condylar part of the femoral component (1), forming an undulating curve across the entire extent thereof in the absence of discontinuities, flats and sharp edge, in a generally sinusoidal configuration, and wherein transversely in a frontal plane, the surface of the femoral component (1), which is directed towards the complementary surface of the insert coming into continuous medio-lateral contact with the insert (3) defines a curve (S1) which includes a hollowed central part (10) having an undulating shape with a concavity which is directed towards the insert and which connects tangentially on opposite sides thereof to the lateral parts (7) of the femoral component (1), forming an undulating curve in the absence of any discontinuities, flats and sharp edges of generally a sinusoidal configuration across the entirety thereof, which follows the surface of the femoral component from its most frontal part to the rearmost part thereof and of the insert, said mutual contact surface of the femoral component (1) being defined by a spiral curve, said spiral curve consisting of a plurality of continuously varying radii along the extent thereof extending in the sagittal plane following said sinusoidal configuration from medial to lateral, and said mutual contact surface of the insert being defined by a spiral curve, said spiral curve consisting of a plurality of continuously varying radii along the extent thereof extending in the sagittal plane in correlation with the configuration of at least a portion of the spiral curve in the sagittal plane of said femoral component.

6. A knee prosthesis, which is implantable in the knee joint of a patient, said prosthesis comprising a femoral component (1) which is implantable in the femur of the knee joint; a tibial component (2) which is implantable in the tibia of the knee joint; and an intermediate insert (3) which is interposed between the tibial component and the femoral component of said prosthesis, said insert being selectively rigidly integral with the tibial component or movable in rotation about a vertical axis relative to the tibial component, said femoral component comprising two lateral parts (7), each with a condylar surface which bears against and is movable in two lateral cavities (8) of a complementary profile provided in the insert, and includes a hollowed central part (10) arranged between said lateral parts and which bears on a projecting central part (9) of the insert, the projecting central part (9) of the insert (3), which is directed toward the femoral component (1) having a convex shape in a frontal plane, and a concave shape in a sagittal plane, the hollowed central part (10) of the femoral component (1) having a concave shape in a frontal plane, and a convex shape in a sagittal plane extending from the front to the rear of the femur of the knee joint, so as to facilitate the femoral component (1) straddling the projecting part (9) of the insert during relative displacements thereof and to cooperate cam-like therewith, said knee prosthesis having the surfaces of the femoral component (1) and of the insert (3) come into mutual surface contact during the relative movements between said femoral component in the absence of any discontinuities, flats and sharp edges and cooperate through the straddling of concave parts and convex parts thereof during the entirety of these movements within, respectively, each of the sagittal and frontal planes, wherein transversely in a frontal plane, the mutual contact surface of the insert (3), which is directed towards the complementary mutual contact surface of the femoral component (1) and coming into continuous medio-lateral contact with the femoral component (1) is a curve (S2) which includes a projecting central part (9) having an inwardly curved central portion possessing a convexity which is directed towards the femoral component (1) and which connects tangentially on opposite sides thereof to each said lateral cavity (8) having a shape corresponding substantially with that of a therewith associated lateral part of the femoral component (1), forming an undulating curve in a generally sinusoidal configuration, and wherein transversely in a frontal plane, the surface of the femoral component (1), which is directed towards the complementary surface of the insert coming into continuous medio-lateral contact with the insert (3) defines a curve (S1)

which includes a hollowed central part (10) having an undulating shape with a concavity which is directed towards the insert and which connects tangentially on opposite sides thereof to the lateral parts (7) of the femoral component (1), forming an undulating curve in the absence of any discontinuities, flats and sharp edges of generally a sinusoidal configuration, which follows the mutual contact surface of the femoral component and of the insert from its most frontal part to the rearmost part thereof, the femoral contact surface of the femoral component being defined by the combination of a spiral curve in the sagittal plane following an undulating curve of sinusoidal type in a frontal plane, said spiral curve consisting of a plurality of continuously varying radii along the extent thereof the contact surface of the insert (3) being defined by the combination of a spiral curve in the sagittal plane in conformance with at least a portion of the spiral curve of the femoral component, said spiral curve consisting of a plurality of continuously varying radii along the extent thereof and of an undulating curve of sinusoidal configuration in the frontal plane, said two surfaces being in a concave-convex engagement in each of said two planes, whereby the two surfaces provide for a continuous transverse medio-lateral contact from complete extension to complete flexion of the prosthesis.

7. The prosthesis as claimed in claim 6, wherein the lateral parts and the hollowed central part (10) of the femoral component (1) extending transversely through at least one sagittal plane, have the shape of a spiral of any geometrical form, said spiral curve consisting of a plurality of continuously varying radii along the extent thereof, and wherein extending transversely through a sagittal plane, the complementary lateral parts (8) and projecting central part (9) of the insert (3) also have the shape of a spiral of any geometrical form, said spiral curve consisting of a plurality of continuously varying radii along the extent thereof.

* * * * *

UNITED STATES PATENT AND TRADEMARK OFFICE
CERTIFICATE OF CORRECTION

PATENT NO. : 6,893,467 B1
DATED : May 17, 2005
INVENTOR(S) : Michel Bercovy

Figure 3:
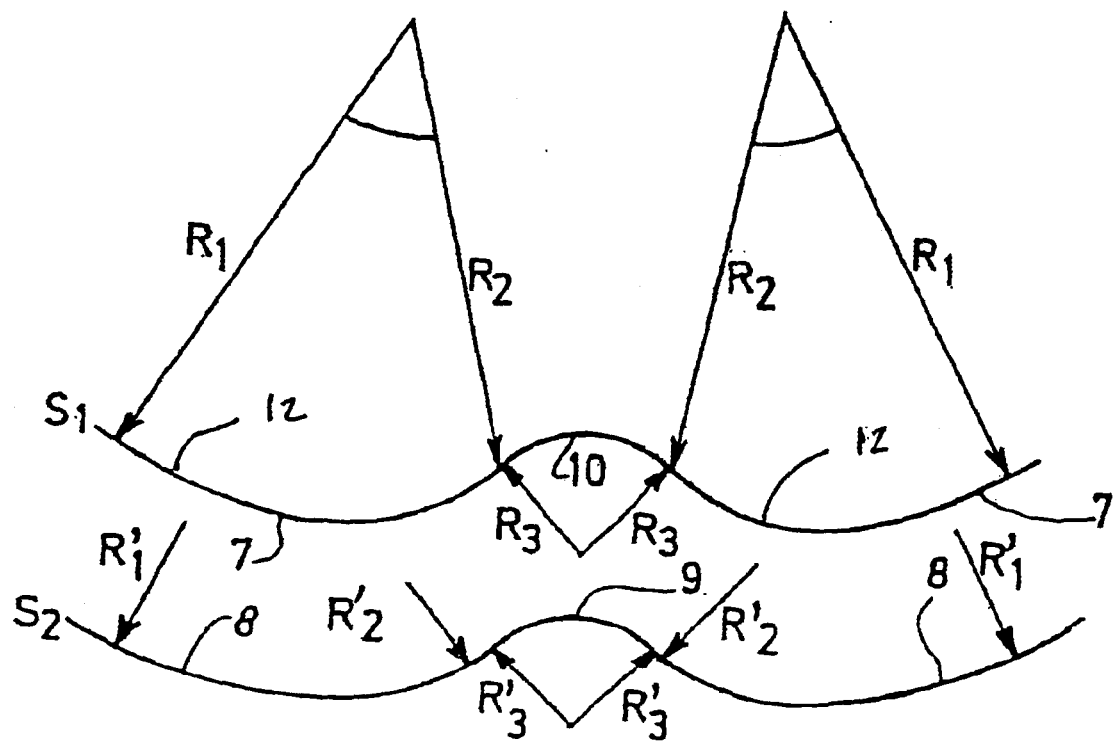

It is certified that error appears in the above-identified patent and that said Letters Patent is hereby corrected as shown below:

Drawings,
Replace drawing Figures 1, 2A, 2B, 3A & 3B with correct drawing Figures 1, 2, & 3, as attached.

Signed and Sealed this

Thirtieth Day of August, 2005

JON W. DUDAS
*Director of the United States Patent and Trademark Office*